(12) United States Patent
Seo et al.

(10) Patent No.: US 9,893,298 B2
(45) Date of Patent: Feb. 13, 2018

(54) ORGANIC LIGHT EMITTING DISPLAY DEVICE

(71) Applicant: LG Display Co., Ltd., Seoul (KR)

(72) Inventors: Jeongdae Seo, Incheon (KR);
ChangWook Han, Seoul (KR);
SungHoon Joo, Gyeonggi-do (KR);
Hyoseok Kim, Daejeon (KR);
Hyeseung Kang, Seoul (KR);
Seonkeun Yoo, Gyeonggi-do (KR);
JungSoo Park, Seoul (KR)

(73) Assignee: LG Display Co., Ltd., Seoul (KR)

( * ) Notice: Subject to any disclaimer, the term of this patent is extended or adjusted under 35 U.S.C. 154(b) by 134 days.

(21) Appl. No.: 14/955,259

(22) Filed: Dec. 1, 2015

(65) Prior Publication Data

US 2016/0164004 A1 Jun. 9, 2016

(30) Foreign Application Priority Data

Dec. 8, 2014 (KR) ........................ 10-2014-0175345
Oct. 16, 2015 (KR) ........................ 10-2015-0144720

(51) Int. Cl.
*C09K 11/02* (2006.01)
*H01L 51/00* (2006.01)
(Continued)

(52) U.S. Cl.
CPC ........ *H01L 51/0072* (2013.01); *C07D 401/10* (2013.01); *C09K 11/025* (2013.01);
(Continued)

(58) Field of Classification Search
CPC ............ H01L 51/0067; H01L 51/0072; H01L 51/0058; H01L 51/5278; C09K 11/025; C07D 401/10
(Continued)

(56) References Cited

U.S. PATENT DOCUMENTS

2007/0222376 A1 9/2007 Ohsawa et al.
2011/0095282 A1 4/2011 Pflumm et al.
(Continued)

FOREIGN PATENT DOCUMENTS

CN 1780019 A 5/2006
CN 102326273 A 1/2012
(Continued)

OTHER PUBLICATIONS

Office Action issued in corresponding Chinese Patent Application No. 201510888139.9 dated Mar. 10, 2017.
(Continued)

*Primary Examiner* — Amanda C Walke
(74) *Attorney, Agent, or Firm* — Morgan, Lewis & Bockius LLP

(57) ABSTRACT

An organic light emitting display device is disclosed. The organic light emitting display device comprises an emitting layer over an anode, the light emitting part having an emitting layer and an electron transporting layer, and a cathode on the light emitting part, wherein each of the emitting layer and the electron transporting layer includes a compound with the same core to facilitate electron transport from the electron transporting layer to the emitting layer.

9 Claims, 2 Drawing Sheets

(51) Int. Cl.
*H01L 27/32* (2006.01)
*H01L 51/50* (2006.01)
*C07D 401/10* (2006.01)
*H01L 51/52* (2006.01)

(52) U.S. Cl.
CPC ...... *H01L 27/3244* (2013.01); *H01L 51/0058* (2013.01); *H01L 51/0067* (2013.01); *H01L 51/5072* (2013.01); *H01L 51/5044* (2013.01); *H01L 51/5056* (2013.01); *H01L 51/5278* (2013.01); *H01L 2251/5315* (2013.01); *H01L 2251/5384* (2013.01)

(58) Field of Classification Search
USPC ............ 544/180; 428/690; 548/304.4, 305.1, 548/361.1; 257/40
See application file for complete search history.

(56) References Cited

U.S. PATENT DOCUMENTS

| | | | |
|---|---|---|---|
| 2011/0156013 A1* | 6/2011 | Kim | C07D 401/10 257/40 |
| 2012/0097899 A1 | 4/2012 | Parham et al. | |
| 2012/0119197 A1* | 5/2012 | Nishimura | C07D 209/86 257/40 |
| 2012/0235123 A1* | 9/2012 | Lee | H01L 51/0072 257/40 |
| 2014/0203272 A1† | 7/2014 | Hong | |
| 2015/0270506 A1* | 9/2015 | Voges | H01L 51/506 257/40 |

FOREIGN PATENT DOCUMENTS

| | | | |
|---|---|---|---|
| CN | 102459507 A | 5/2012 | |
| CN | 103827256 A | 5/2014 | |
| WO | 2014/104665 A1 | 7/2014 | |
| WO | 2014/142488 A1 | 9/2014 | |
| WO | 2014/166577 A1 | 10/2014 | |
| WO | WO 2015175678 A1 * | 11/2015 | ............ C09K 11/06 |

OTHER PUBLICATIONS

Extended European Search Report dated Apr. 18, 2016 issued by the European Patent Office in corresponding European Patent Application No. 15194113.5.

Chen et al., "1,3,5-Triazine derivatives as new electron transport-type host materials for highly efficient green phosphorescent OLEDs", J. Mater. Chem., 19:8112-8118 (2009).

Hung et al., "Highly Efficient Bilayer Interface Exciplex for Yellow Organic Light-Emitting Diode", ACS Appl. Mater. Interfaces, 5:6826-6831 (2013).

Hung et al., "The First Tandem, All-exciplex-based WOLED", Scientific Reports, 4:1-6 (2014).

Zhang et al., "Low-driving voltage blue, green, yellow, red and white organic light-emitting diodes with a simply double light-emitting structure", Optics Express, 22:1815-1823 (2014).

\* cited by examiner
† cited by third party

ORGANIC LIGHT EMITTING DISPLAY DEVICE

This application claims the benefit of Korean Patent Application Nos. 10-2014-0175345 filed on Dec. 8, 2014, and 10-2015-0144720 filed on Oct. 16, 2015, which are hereby incorporated herein by reference for all purposes as if fully set forth herein.

BACKGROUND OF THE INVENTION

Field of the Invention

The present invention relates to an organic light emitting display device, and more particularly, to an organic light emitting display device having reduced operating voltage and improving external quantum efficiency and lifetime.

Discussion of the Related Art

Image displays used for displaying a variety of information on the screen are one of the core technologies of the information and communication era. Such image displays have been developed to be thinner, lighter, and more portable, and furthermore to have high performance. With the development of the information society, various demands for display devices are on the rise. To meet these demands, research on flat panel displays such as liquid crystal displays (LCD), plasma display panels (PDP), electroluminescent displays (ELD), field emission displays (FED), organic light emitting diodes (OLED), etc is actively under way.

Among these types of panel displays, the OLED devices are advantageous in that they can be on a flexible substrate such as plastic, can be driven at a low voltage of 10 V or less, less power consumption, and shows an excellent color sense, as compared with plasma display panels or inorganic EL displays. Also, the organic light emitting display devices are spotlighted as next-generation display devices that render rich colors since they can represent three colors: red, green, and blue.

An organic light emitting device can be formed by sequentially stacking an anode, a hole injection layer, a hole transport layer, an emitting layer, an electron transport layer, an electron injection layer, and a cathode. An exciton is formed by the recombination of electrons and holes injected from the two electrodes, causing luminescent materials to emit fluorescent or phosphorescent light. The emitting layer comprises a host and one or more dopants, or comprises two or more hosts and a dopant. Recently, a hole-type host and an electron-type host are used in mixture, in order to enhance injection of holes and electrons into the emitting layer. The electron transport layer injects electrons from the cathode into the emitting layer, and the hole injection layer injects holes from the anode into the emitting layer.

However, the electron-type host material for the emitting layer and the electron transport layer material have different structures, which results in a barrier too large for electron injection from the electron transport layer into the emitting layer. This leads to a lack of electrons to be injected into the emitting layer, thus increasing the operating voltage of the device and decreasing its efficiency and lifetime.

SUMMARY

Accordingly, the present invention is directed to an organic light emitting display device that substantially obviates one or more of the problems due to limitations and disadvantages of the related art.

An object of the present invention is to provide an organic light emitting display device which is capable of reducing operating voltage and improving external quantum efficiency and lifetime.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, an organic light emitting display device comprises a first light emitting part between an anode and a cathode, the first light emitting part having a first emitting layer and a first electron transport layer, and a second light emitting part over the first light emitting part, the second light emitting part having a second emitting layer and a second electron transport layer, wherein at least one among the first and second emitting layers includes a compound represented by the following Chemical Formula 1, and at least one among the first and second electron transport layers includes a compound represented by the following Chemical Formula 2 or Chemical Formula 3:

[Chemical Formula 1]

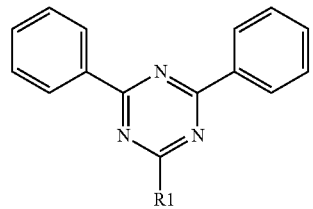

where R1 is a ring system comprising one or more an aromatic ring and/or heteroaromatic rings having at least one heteroatom among N, O, S, and Si, wherein the ring system has a total number of 6 to 60 carbon atoms,

[Chemical Formula 2]

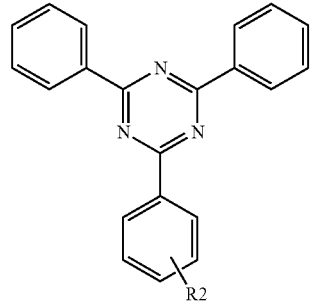

where R2 is a ring system comprising one or more an aromatic ring and/or heteroaromatic rings having at least one heteroatom among N, O, S, and Si, wherein the ring system has a total number of 6 to 60 carbon atoms,

[Chemical Formula 3]

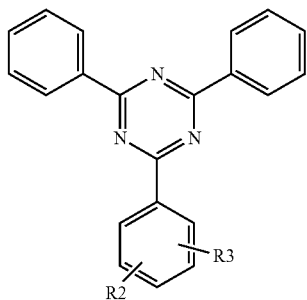

where R2 and R3 are independently a ring system comprising one or more aromatic ring and/or heteroaromatic rings having at least one heteroatom among N, O, S, and Si, wherein the ring system has a total number of 6 to 60 carbon atoms, and R2 and R3 are the same or the different each other.

In another aspect, an organic light emitting display device comprises a light emitting part over an anode, the light emitting part having an emitting layer and an electron transport layer, and a cathode over the light emitting part, wherein the emitting layer and the electron transport layer include a compound with the same core to facilitate electron transport from the electron transport layer to the emitting layer.

It is to be understood that both the foregoing general description and the following detained description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE ILLUSTRATED EMBODIMENTS

Figure 1:
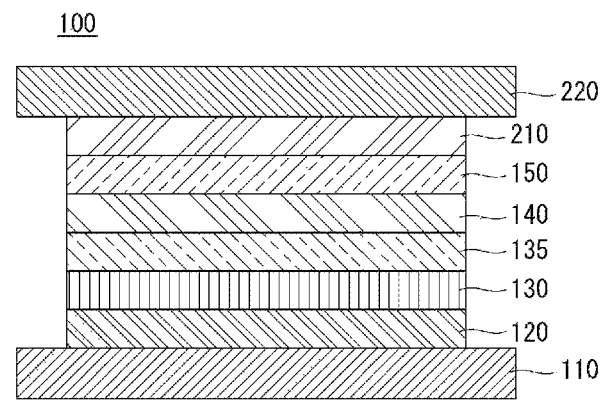
FIG. 1 is a cross-sectional view showing an organic light emitting display device according to a first exemplary embodiment of the present invention.

The advantages and features of the present invention and methods for accomplishing the same may be understood more readily by reference to the following detailed descriptions of exemplary embodiments and the accompanying drawings. The present invention may, however, be embodied in many different forms and should not be construed as being limited to the exemplary embodiments set forth herein. Rather, these exemplary embodiments are provided so that this disclosure will be thorough and complete and will fully convey the concept of the present invention to those skilled in the art, and the present invention is defined by the appended claims The shapes, sizes, percentages, angles, numbers, etc shown in the figures to describe the exemplary embodiments of the present invention are merely examples and not limited to those shown in the figures. Like reference numerals denote like elements throughout the specification. In describing the present invention, detailed descriptions of related well-known technologies will be omitted to avoid unnecessary obscuring the present invention. When the terms 'comprise', 'have', 'consist of' and the like are used, other parts may be added as long as the term 'only' is not used. The singular forms may be interpreted as the plural forms unless explicitly stated.

The elements may be interpreted to include an error margin even if not explicitly stated.

When the position relation between two parts is described using the terms 'on', 'over', 'under', 'next to' and the like, one or more parts may be positioned between the two parts as long as the term 'immediately' or 'directly' is not used.

When the temporal relationship between two events is described using the terms 'after', 'following', 'next', 'before' and the like, the two events may not occur in succession as long as the term 'immediately' or 'directly' is not used.

It will be understood that, although the terms first, second, etc., may be used to describe various elements, these elements should not be limited by these terms. These terms are only used to distinguish one element from another element. Thus, a first element discussed below could be termed a second element without departing from the technical spirit of the present invention.

The features of various exemplary embodiments of the present invention may be combined with one another either partly or wholly, and may technically interact or work together in various ways. The exemplary embodiments may be carried out independently or in combination with one another.

Hereinafter, various exemplary embodiments of the present invention will be described in detail with reference to the accompanying drawings.

FIG. 1 is a cross-sectional view showing an organic light emitting display device according to a first exemplary embodiment of the present invention.

With reference to the example of FIG. 1, an organic light emitting display device 100 according to the present invention comprises organic films 120, 130, 135, 140, 150, and 210 between an anode 110 and a cathode 220. The anode 110 is a hole injection electrode, and may be formed of ITO (indium tin oxide), IZO (indium zinc oxide), or ZnO (zinc oxide) having a high work function. Also, if the anode 110 is a reflective electrode, the anode 110 may further comprise a reflective layer formed of aluminum (Al), silver (Ag), or nickel (Ni) under a layer formed one among ITO, IZO, or ZnO.

A hole injection layer 120 is over the anode 110. The hole injection layer 120 may function to facilitate hole injection from the anode 110 to an emitting layer 140, and may be formed of, but is not limited to, one among CuPc (copper phthalocyanine), PEDOT (poly(3,4)-ethylenedioxythiophene), PANI (polyaniline), and NPD ((N,N'-bis(naphthalene-1-yl)-N,N'-bis(phenyl)-2,2'-dimethylbenzidine). The hole injection layer 120 may be 1 to 150 nm thickness. If the hole injection layer 120 is 1 nm thickness or greater, the hole injection properties may be improved, or if the hole injection layer 120 is 150 nm thickness or less, an increase in the thickness of the hole injection layer 120 may be prevented and a rise in operating voltage may be therefore prevented. The hole injection layer 120 may not be included in the composition of the organic light emitting display device, depending on the structure or characteristics of the organic light emitting display device.

A hole transport layer 130 is over the hole injection layer 120. The hole transport layer 130 may function to facilitate hole transport, and may be formed of, but is not limited to, one among NPD (N,N'-bis(naphthalene-1-yl)-N,N'-bis(phenyl)-2,2'-dimethylbenzidine), TPD (N,N'-bis-(3-methylphenyl)-N,N'-bis(phenyl)-benzidine), spiro-TAD (2,2'7,7'-tetrakis(N,N-diphenylamino)-9,9'-spirofluorene), and MTDATA (4,4',4"-Tris(N-3-methylphenyl-N-phenylamino)-triphenylamine). The hole transport layer 130 may be 1 to 150 nm thickness. If the hole transport layer 130 is 1 nm thickness or greater, the hole transport properties may be improved, or if the hole transport layer 130 is 150 nm thickness or less, an increase in the thicknesses of the hole transport layer 130 may be prevented and a rise in operating voltage may be therefore prevented.

An electron blocking layer 135 is over the hole transport layer 130. The electron blocking layer 135 functions to block electrons injected from the cathode 220 from getting to the anode 110, and may be formed of, but is not limited to, one among TPD (N,N'-bis-(3-methylphenyl)-N,N'-bis (phenyl)-benzidine), NPD (N,N'-bis(naphthalene-1-yl)-N, N'-bis(phenyl)-2,2'-dimethylbenzidine), TCTA (4,4'4"-tris) carbozoyl-9-yl)triphenylamine), and CBP (4,4'-bis (carbazol-9-yl)biphenyl. The electron blocking layer 135 may not be included in the composition of the organic light emitting display device, depending on the structure or characteristics of the organic light emitting display device. A hole blocking layer may be formed on the emitting layer 140.

The emitting layer 140 is over the electron blocking layer 135. The emitting layer 140 may emit light one among red (R), green (G), or blue (B), and may be formed of a phosphorescent material. The emitting layer 140 comprises a host(s) and a dopant(s). The host serves to transfer energy to the dopant. Hosts of the present invention comprise an electron-type host and a hole-type host. Examples of the hole-type host may include one among NPB (N,N'-bis (naphthalene-1-yl)-N,N'-bis(phenyl)-benzidine), CBP (4,4'-bis(carbazol-9-yl)biphenyl), TPD (N,N'-bis(3-methylphenyl)-N,N'-bis(phenyl)-benzidine), spiro-TAD (2,2'7,7'-tetrakis(N,N-diphenylamino)-9,9'-spirofluorene), MTDATA (4,4',4"-Tris(N-3-methylphenyl-N-phenylamino)-triphenylamine), and so on.

In the present invention, a heteroaromatic ring compound is applied as the electron-type host, in order to improve the property of transporting electrons to the emitting layer. The heteroaromatic ring compound including a triazine having 3 nitrogen atoms that are electron-rich improves the electron transport properties in the emitting layer. In the present invention, a heteroaromatic ring compound with electron transport properties is applied as the electron-type host for the emitting layer, thus making the emitting layer rich in electrons and reducing the operating voltage of the device and increasing its efficiency and lifetime.

Accordingly, the electron-type host for the emitting layer 140 of this invention includes a heteroaromatic ring compound represented by the following Chemical Formula 1:

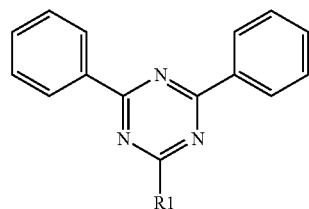

[Chemical Formula 1]

where R1 is a ring system comprising one or more aromatic ring and/or heteroaromatic rings having at least one heteroatom among N, O, S, and Si, wherein the ring system has a total number of 6 to 60 carbon atoms.

The heteroaromatic ring compound represented by Chemical Formula 1 includes one among the following compounds:

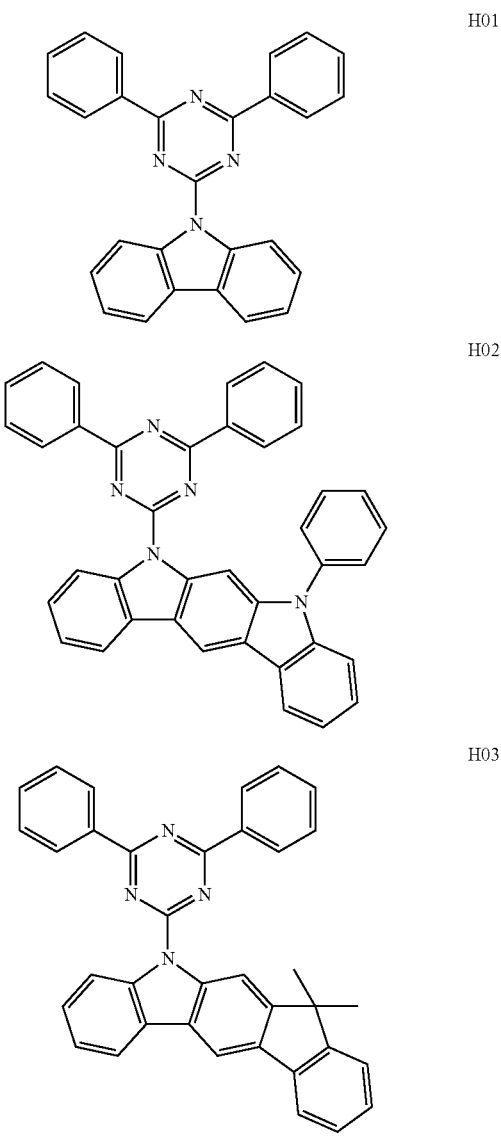

H04

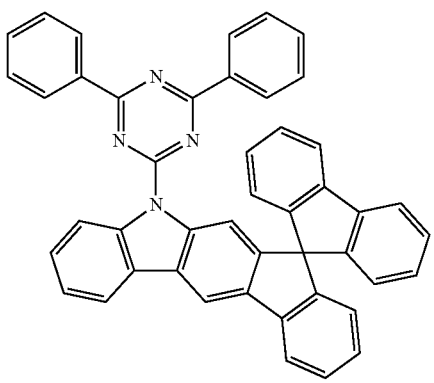

H05

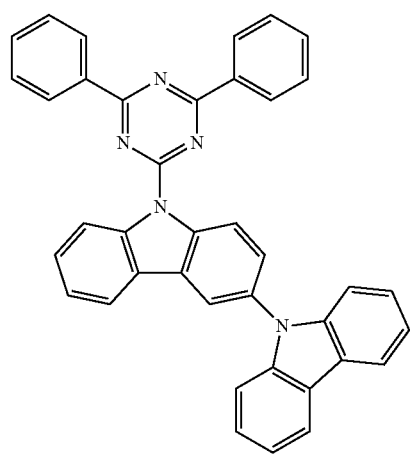

H06

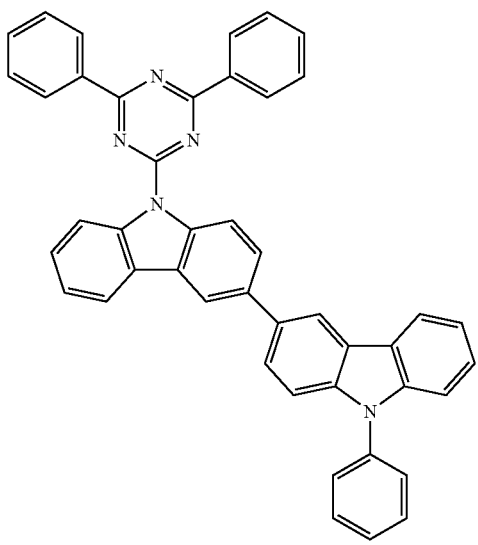

H07

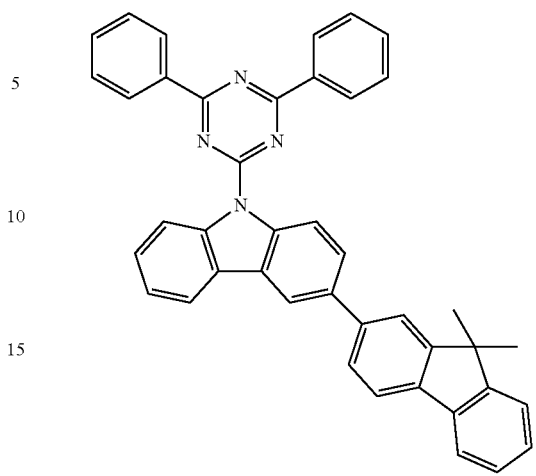

H08

An electron transport layer 150 is over the emitting layer 140. The electron transport layer 150 facilitates electron transport to the emitting layer 140. In the present invention, a heteroaromatic ring compound is applied as the electron transport layer 150, in order to improve the property of transporting electrons to the emitting layer 140. As the heteroaromatic ring compound comprises a triazine having 3 nitrogen atoms that are electron-rich, it improves the property of transporting electrons from the electron transport layer 150 to the emitting layer 140. Especially, the heteroaromatic ring compound as the electron transport layer 150 of the present invention has the same core structure as the heteroaromatic ring compound as the aforementioned electron-type host material for the emitting layer 140. That is, the emitting layer 140 and the electron transport layer 150 having the compound with the same core structure facilitate electron transport from the electron transport layer 150 to the emitting layer 140. The compound with the same core may be a heteroaromatic ring compound. Alternatively, the compound with the same core may be a heteroaromatic ring compound having a triazine. Also, the emitting layer 140 may comprise an electron-type host and a hole-type host, and the electron-type host may include the compound with the same core. As the heteroaromatic ring compound as a host for the emitting layer 140 and the heteroaromatic ring compound as the electron transport layer 150 have the same core structure, the host for the emitting layer 140 and the electron transport layer 150 has a similar energy level, facilitating electron transport from the electron transport layer 150 to the emitting layer 140. Accordingly, the present invention can reduce the operating voltage of the device and increase its efficiency and lifetime through an improvement in the electron transport from the electron transport layer to the emitting layer by lowering a barrier of the electron injection of the electron transport layer and the emitting layer, by applying a heteroaromatic ring compound with the same core as a host material for the emitting layer and the material of the electron transport layer.

Accordingly, the electron transport layer 150 of the present invention includes a heteroaromatic ring compound represented by the following Chemical Formula 2 or Chemical Formula 3:

[Chemical Formula 2]

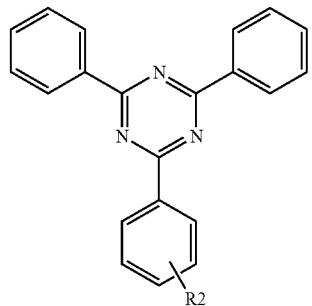

where R2 is a ring system comprising one or more aromatic ring and/or heteroaromatic rings having at least one heteroatom among N, O, S, and Si, wherein the ring system has a total number of 6 to 60 carbon atoms,

[Chemical Formula 3]

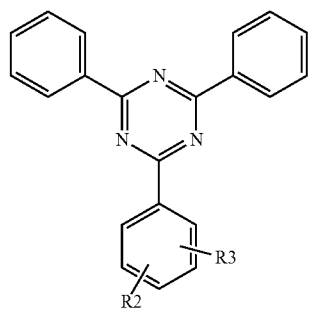

where R2 and R3 are independently a ring system comprising one or more aromatic ring and/or heteroaromatic rings having at least one heteroatom among N, O, S, and Si, wherein the ring system has a total number of 6 to 60 carbon atoms, and R2 and R3 are the same or the different each other.

The heteroaromatic ring compound represented by Chemical Formula 2 includes one among the following compounds E01, E02, E04, and E05, the heteroaromatic ring compound represented by Chemical Formula 3 includes one among the following compounds E03, E06, E07, E08, E09, and E10:

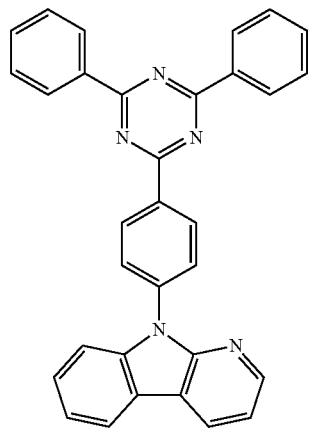

E01

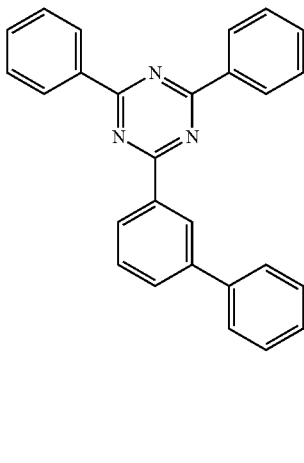

E02

E03

E04
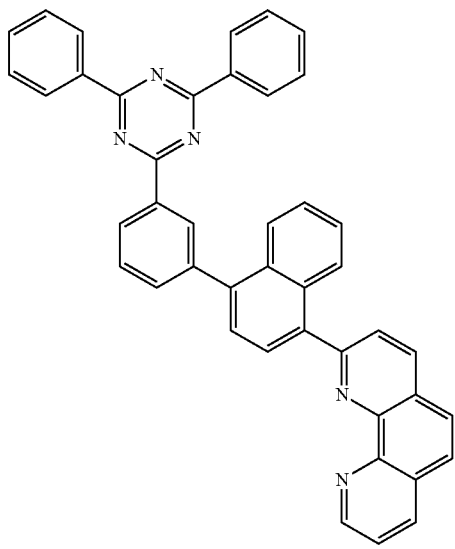
E05
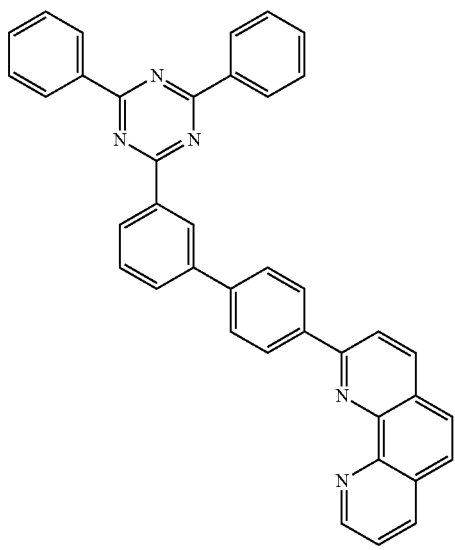
E06
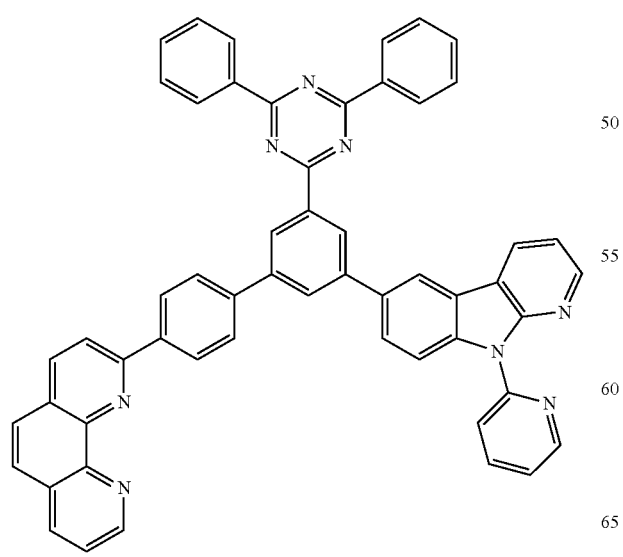
E07
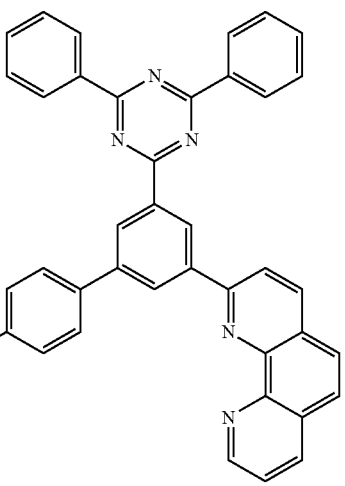
E08
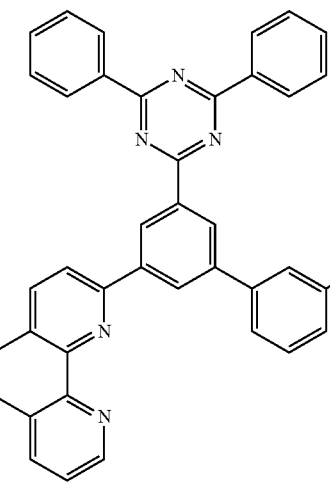
E09
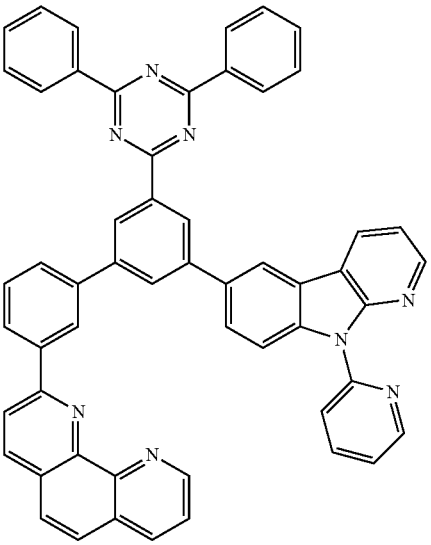

E10

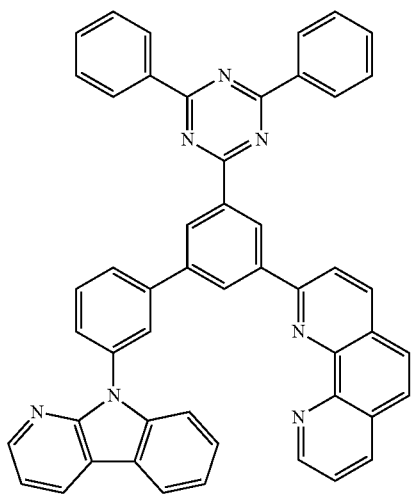

In the present invention, the host material for the emitting layer and the material for the electron transport layer include a heteroaromatic compound with the same core. The emitting layer emits light by the recombination of holes received from the hole transport layer and electrons received from the electron transport layer. For example, the emitting layer may include a hole-type host and an electron-type host. The electron-type host in the emitting layer transfers electrons received from the electron transport layer to the emitting layer. Accordingly, the electron-type host requires stability for holes because both holes and electrons are distributed within the emitting layer, and has to smoothly transfer electrons or holes, which are excitons or carriers, to the dopant included in the emitting layer. The electron transport layer is also required to block excitons and holes from the electron transport layer to the emitting layer.

As a way to develop materials that satisfy the characteristics required for the emitting layer and the electron transport layer, the development of compounds with various core structures regardless of a particular core structure can reduce the development cost and time. However, the electron-type host of the emitting layer and the electron transport layer may be formed of materials with a similar core structure because they role as a common to facilitate electron transfer. If compounds with a similar core structure are used as the host material for the emitting layer and the material for the electron transport layer, the electron injection barrier at the interface between the emitting layer and the electron transport layer can be lowered, offering advantages in electron movement or electron transport. Accordingly, in the present invention, compounds with the same core structure may be used as the host material for the emitting layer and the material for the electron transport layer.

The electron transport layer 150 may be 1 to 150 nm thickness. If the electron transport layer 150 is 1 nm thickness or greater, the electron transport properties may be improved, or if the electron transport layer 150 is 150 nm thickness or less, an increase in the thicknesses of the electron transport layer 150 may be prevented and a rise in operating voltage may be therefore prevented.

An electron injection layer 210 is over the electron transport layer 150. The electron injection layer 210 functions to facilitate electron injection, and may be formed of, but is not limited to, one among $Alq_3$ (tris(8-hydroxyquinolinato)aluminum), PBD (2-4-biphenyl)-5-(4-tert-butylphenyl)-1,3,4-oxadiazole), TAZ (3-(4-biphenyl)-4-pheynyl-5-tert-butylphenyl-1,2,4-triazole), or BAlq (Bis(2-methyl-8-quinolinolate)-4-(phenylphenolato)aluminum). On the other hand, the electron injection layer 210 may be formed of a metal compound, and the metal compound may be, for example, but is not limited to, one among LiQ, LiF, NaF, KF, RbF, CsF, FrF, $BeF_2$, $MgF_2$, $CaF_2$, $SrF_2$, $BaF_2$, and $RaF_2$. The electron injection layer 210 may be 1 to 50 nm thickness. If the electron injection layer 210 is 1 nm thickness or greater, a degradation of the electron injection properties may be prevented, or if the electron injection layer 210 is 50 nm thickness or less, an increase in the thickness of the electron injection layer 210 may be prevented and a rise in operating voltage may be therefore prevented.

The cathode 220 is an electron injection electrode, and may be formed of one among magnesium (Mg), calcium (Ca), aluminum (Al), silver (Ag), or an alloy thereof, having a low work function. If the organic light emitting display device is a top-emission type or a dual-emission type, the cathode 220 may be formed thin enough to pass light therethrough. If the organic light emitting display device is a bottom-emission type, the cathode 220 may be formed thickness enough to reflect light.

The present invention is used a heteroaromatic ring compound including a triazine having 3 electron-rich nitrogen atoms as the electron-type host, thereby improving the property of transporting electrons to the emitting layer.

Also, the present invention is used a heteroaromatic ring compound with electron transport properties as the electron-type host for the emitting layer, thus making the emitting layer rich in electrons, thereby reducing the operating voltage of the device and increasing its efficiency and lifetime.

Moreover, the present invention is used a triazine having 3 electron-rich nitrogen atoms as the electron transport layer, thus improving the property of transporting electrons from the electron transport layer to the emitting layer.

In addition, the present invention is used heteroaromatic ring compounds with the same core are used as the host material for the emitting layer and the material for the electron transport layer, thus allowing the host for the emitting layer and the electron transport layer to have a similar energy level and therefore facilitating electron transport from the electron transport layer to the emitting layer.

Further, the present invention is used heteroaromatic ring compounds with the same core as the host material for the emitting layer and the material for the electron transport layer, thus lowering the electron injection barrier between the electron transport layer and the emitting layer and therefore improving the property of transporting electrons from the electron transport layer to the emitting layer.

Further, the present invention is used heteroaromatic ring compounds with the same core as the host material for the emitting layer and the material for the electron transport layer, thus improving the property of transporting electrons from the electron transport layer to the emitting layer and therefore reducing the operating voltage of the organic light emitting device and increasing its efficiency and lifetime.

Figure 2:
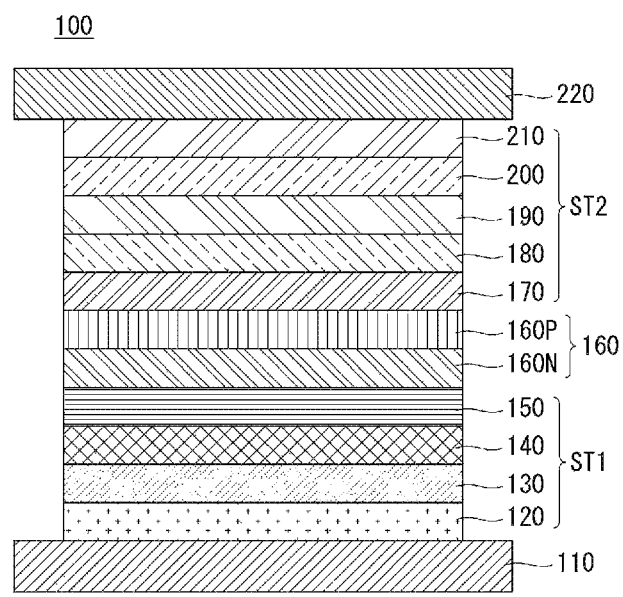
FIG. 2 is a cross-sectional view showing an organic light emitting display device according to a second exemplary embodiment of the present invention.

FIG. 2 is a view showing an organic light emitting display device according to a second exemplary embodiment of the present invention. The same elements as the first exemplary embodiment are denoted by the same reference numerals, so descriptions of these elements will be omitted below.

In the example of FIG. 2, an organic light emitting display device 100 of the present invention comprises a plurality of light emitting parts ST1 and ST2 between an anode 110 and a cathode 220, and a charge generation layer 160 between the light emitting parts ST1 and ST2. The light emitting part is a single light emitting diode unit.

More specifically, the first light emitting part ST1 comprises a first emitting layer 140. The first emitting layer 140 may emit light of red, green, or blue: for example, it may be a blue emitting layer in this exemplary embodiment. The first light emitting part ST1 further comprises a first hole injection layer 120 and a first hole transport layer 130 that are between the anode 110 and the first emitting layer 140. Also, the first light emitting part ST1 further comprises a first electron transport layer 150 over the first emitting layer 140. Accordingly, the first light emitting part ST1 comprising the first hole injection layer 120, the first hole transport layer 130, the first emitting layer 140, and the first electron transport layer 150 is formed over the anode 110. The first hole injection layer 120 may not be included in the composition of the first light emitting part ST1, depending on the structure or characteristics of the device. Besides, an electron blocking layer may be formed over the first hole transport layer 130, and a hole blocking layer may be formed over the first emitting layer 140.

The second light emitting part ST2 having a second emitting layer 190 is over the charge generation layer 160. The second emitting layer 190 may emit light of red, green, or blue, and it may be a yellow emitting layer, for example, in this exemplary embodiment. The yellow emitting layer may comprise a yellow-green emitting layer, a green emitting layer, or a multilayer structure of a yellow-green emitting layer and a green emitting layer. The second light emitting part ST2 further comprises a second hole injection layer 170 and a second hole transport layer 180 that are on the first light emitting part ST1. Also, the second light emitting part ST2 further comprises a second electron transport layer 200 and an electron injection layer 210 that are over the second emitting layer 190. Accordingly, the second light emitting part ST2 comprising the second hole injection layer 170, the second hole transport layer 180, the second emitting layer 190, the second electron transport layer 200, and the electron injection layer 210 is formed over the charge generation layer 160. The second hole injection layer 170 or the electron injection layer 210 may not be included in the composition of the second light emitting part ST2 depending on the structure or characteristics of the device. Besides, an electron blocking layer may be formed over the second hole transport layer 180, and a hole blocking layer may be formed over the second emitting layer 190.

A charge generation layer (CGL) 160 is between the first light emitting part ST1 and the second light emitting part ST2. The first light emitting part ST1 and the second light emitting part ST2 are connected by the charge generation layer 160. The charge generation layer 160 may be a PN-junction charge generation layer formed by joining an N-type charge generation layer 160N and a P-type charge generation layer 160P. The PN-junction charge generation layer 160 generates a charge, or injects the charge, i.e., electrons and holes, separately into the emitting layers. That is, the N-type charge generation layer 160N supplies electrons to the first emitting layer 140, which is close to the anode, and the P-type charge generation layer 160P supplies holes to the emitting layer of the second light emitting part ST2. As such, the organic light emitting display device with a plurality of emitting layers can further increase its emission efficiency and decrease its operating voltage.

The N-type charge generation layer 160N may be formed of a metal or an N-doped organic material. The metal may be one among Li, Na, K, Rb, Cs, Mg, Ca, Sr, Ba, La, Ce, Sm, Eu, Tb, Dy, and Yb. An N-type dopant and host for the N-doped organic material may be commonly-used materials. For example, the N-type dopant may be an alkali metal, an alkali metal compound, an alkali earth metal, or an alkali earth metal compound. Specifically, the N-type dopant may be one among Li, Cs, K, Rb, Mg, Na, Ca, Sr, Eu, and Yb. The percentage of the dopant to be mixed is between 1 and 8% relative to 100% for the host. The dopant may have a work function of 2.5 eV or greater. The host material may be an organic material that has a nitrogen atom-having hetero ring, with 20 to 60 carbon atoms, for example, one among tris(8-hydroxyquinoline)aluminum, triazine, a hydroxyquinoline derivative, a benzazole derivative, and a silole derivative.

The P-type charge generation layer 160P may be formed of a metal or a P-doped organic material. The metal may be one or more alloys of Al, Cu, Fe, Pb, Zn, Au, Pt, W, In, Mo, Ni, and Ti. A P-type dopant and host for the P-doped organic material may be commonly-used materials. For example, the P-type dopant may be one among $F_4$-TCNQ (2,3,5,6-tetrafluoro-7,7,8,8,-tetracyanoquinodemethane), a derivative of tetracyanoquinodemethane, iodine, $FeCl_3$, $FeF_3$, and $SbCl_5$. The host may be one among NPB (N,N'-bis(naphthalene-1-yl)-N,N'-bis(phenyl)-benzidine), TPD (N,N'-bis-(3-methylphenyl)-N,N'-bis(phenyl)-benzidine), and TNB (N,N,N'N'-tetranaphthalenyl-benzidine).

The cathode 220 is formed over the second light emitting part ST2, thereby constituting the organic light emitting display device according to the second exemplary embodiment of the present invention.

The present invention is used a heteroaromatic ring compound including a triazine having 3 electron-rich nitrogen atoms as the electron-type host, thereby improving the property of transporting electrons to the emitting layer.

Also, the present invention is used a heteroaromatic ring compound with electron transport properties as the electron-type host for the emitting layer, thus making the emitting layer rich in electrons, thereby reducing the operating voltage of the device and increasing its efficiency and lifetime.

Moreover, the present invention is used a triazine having 3 electron-rich nitrogen atoms as the electron transport layer, thus improving the property of transporting electrons from the electron transport layer to the emitting layer.

In addition, the present invention is used heteroaromatic ring compounds with the same core are used as the host material for the emitting layer and the material for the electron transport layer, thus allowing the host for the emitting layer and the electron transport layer to have a similar energy level and therefore facilitating electron transport from the electron transport layer to the emitting layer.

Further, the present invention is used heteroaromatic ring compounds with the same core as the host material for the emitting layer and the material for the electron transport layer, thus lowering the electron injection barrier between the electron transport layer and the emitting layer and therefore improving the property of transporting electrons from the electron transport layer to the emitting layer.

Further, the present invention is used heteroaromatic ring compounds with the same core as the host material for the emitting layer and the material for the electron transport layer, thus improving the property of transporting electrons from the electron transport layer to the emitting layer and therefore reducing the operating voltage of the organic light emitting device and increasing its efficiency and lifetime.

Figure 3:
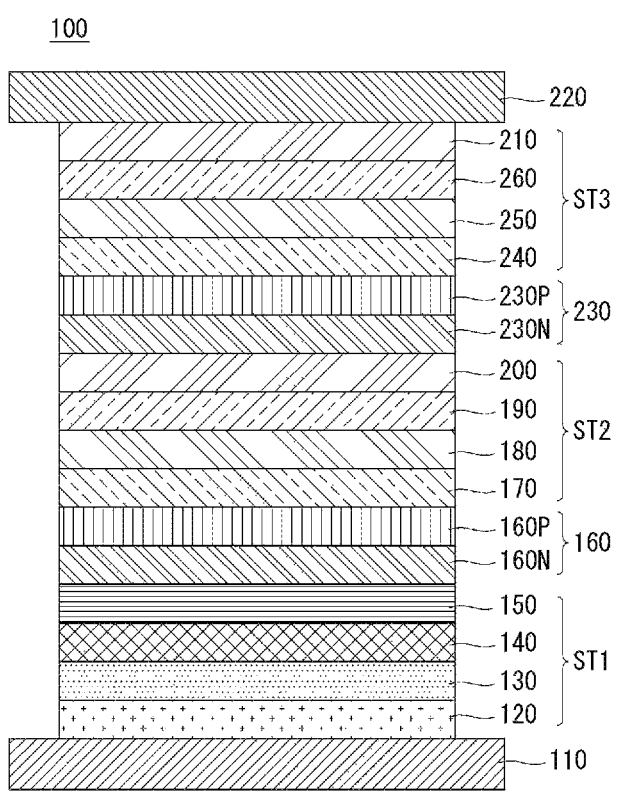
FIG. 3 is a cross-sectional view showing an organic light emitting display device according to a third exemplary embodiment of the present invention.

FIG. 3 is a view showing an organic light emitting display device according to a third exemplary embodiment of the present invention. The same elements as the first and second exemplary embodiments are denoted by the same reference numerals, so descriptions of these elements will be omitted below.

With reference to the example of FIG. 3, an organic light emitting display device 100 of the present invention comprises a plurality of light emitting parts ST1, ST2, and ST3 between an anode 110 and a cathode 220, and a first charge generation layer 160 and a second charge generation layer 230 that are between the light emitting parts ST1, ST2, and ST3. Although this exemplary embodiment has been illustrated and described with an example where three light emitting parts are between the anode 110 and the cathode 220, the present invention is not limited to this example and four or more light emitting parts may be between the anode 110 and the cathode 220. The light emitting part is a single light emitting diode unit.

More specifically, the first light emitting part comprises a first emitting layer 140. The first emitting layer 140 may emit light of red, green, or blue: for example, it may be a blue emitting layer in this exemplary embodiment. The first light emitting part ST1 further comprises a first hole injection layer 120 and a first hole transport layer 130 that are between the anode 110 and the first emitting layer 140. Also, the first light emitting part ST1 further comprises a first electron transport layer 150 over the first emitting layer 140. Accordingly, the first light emitting part ST1 comprising the first hole injection layer 120, the first hole transport layer 130, the first emitting layer 140, and the first electron transport layer 150 is formed over the anode 110. The first hole injection layer 120 may not be included in the composition of the first light emitting part ST1, depending on the structure or characteristics of the device. Besides, an electron blocking layer may be formed over the first hole transport layer 130, and a hole blocking layer may be formed over the first emitting layer 140.

The second light emitting part ST2 comprising a second emitting layer 190 is over the first light emitting part ST1. The second emitting layer 190 may emit light of red, green, or blue, and it may be a yellow emitting layer, for example, in this exemplary embodiment. The yellow emitting layer may comprise a yellow-green emitting layer, a green emitting layer, or a multilayer structure of a yellow-green emitting layer and a green emitting layer. The second light emitting part ST2 further comprises a second hole injection layer 170 and a second hole transport layer 180 that are between the first charge generation layer 160 and the second emitting layer 190, and a second electron transport layer 200 over the second emitting layer 190. Accordingly, the second light emitting part ST2 comprising the second hole injection layer 170, the second hole transport layer 180, the second emitting layer 190, and the second electron transport layer 200 is formed over the first charge generation layer 160. The second hole injection layer 170 may not be included in the composition of the second light emitting part ST2 depending on the structure or characteristics of the device. Besides, an electron blocking layer may be formed over the second hole transport layer 180, and a hole blocking layer may be formed over the second emitting layer 190.

The first charge generation layer 160 is between the first light emitting part ST1 and the second light emitting part ST2. The first charge generation layer 160 is a PN-junction charge generation layer, formed by joining an N-type charge generation layer 160N and a P-type charge generation layer 160P, which generates a charge, or injects the charge, i.e., electrons and holes, separately into the emitting layers.

The third light emitting part ST3 comprising a third emitting layer 250 is over the second light emitting part ST2.

The third emitting layer 250 may emit light of red, green, or blue: for example, it may be a blue emitting layer in this exemplary embodiment. The blue emitting layer comprises a blue emitting layer, a dark blue emitting layer, or a sky blue emitting layer. The third light emitting part ST3 further comprises a third hole transport layer 240 between the second charge generation layer 230 and the third emitting layer 250, and a third electron transport layer 260 and an electron injection layer 210 that are over the third emitting layer 250. The third electron transport layer 260 has the same composition as the aforementioned first electron transport layer 150, so its description will be omitted. Accordingly, the third light emitting part ST3 comprising the third hole transport layer 240, the third emitting layer 250, the third electron transport layer 260, and the electron injection layer 210 is formed over the second charge generation layer 230. The electron injection layer 210 may not be included in the composition of the third light emitting part ST3 depending on the structure or characteristics of the device. Besides, an electron blocking layer may be formed over the third hole transport layer 240, and a hole blocking layer may be formed over the third emitting layer 250.

The second charge generation layer 230 is between the second light emitting part ST2 and the third light emitting part ST3. The second charge generation layer 230 is a PN-junction charge generation layer, formed by joining an N-type charge generation layer 230N and a P-type charge generation layer 230P, which generates a charge, or injects the charge, i.e., electrons and holes, separately into the emitting layers. The N-type charge generation layer 230N has the same composition as the N-type charge generation layer 160N of the first charge generation layer 160, so its description will be omitted. The P-type charge generation layer 230P also has the same composition as the aforementioned P-type charge generation layer 160P of the first charge generation layer 160.

The cathode 220 is formed over the third light emitting part ST3 to constitute the organic light emitting display device according to the third exemplary embodiment of the present invention.

The present invention is used a heteroaromatic ring compound including a triazine having 3 electron-rich nitrogen atoms as the electron-type host, thereby improving the property of transporting electrons to the emitting layer.

Also, the present invention is used a heteroaromatic ring compound with electron transport properties as the electron-type host for the emitting layer, thus making the emitting layer rich in electrons, thereby reducing the operating voltage of the device and increasing its efficiency and lifetime.

Moreover, the present invention is used a triazine having 3 electron-rich nitrogen atoms as the electron transport layer, thus improving the property of transporting electrons from the electron transport layer to the emitting layer.

In addition, the present invention is used heteroaromatic ring compounds with the same core are used as the host material for the emitting layer and the material for the electron transport layer, thus allowing the host for the emitting layer and the electron transport layer to have a similar energy level and therefore facilitating electron transport from the electron transport layer to the emitting layer.

Further, the present invention is used heteroaromatic ring compounds with the same core as the host material for the emitting layer and the material for the electron transport layer, thus lowering the electron injection barrier between the electron transport layer and the emitting layer and therefore improving the property of transporting electrons from the electron transport layer to the emitting layer.

Further, the present invention is used heteroaromatic ring compounds with the same core as the host material for the emitting layer and the material for the electron transport layer, thus improving the property of transporting electrons from the electron transport layer to the emitting layer and therefore reducing the operating voltage of the organic light emitting device and increasing its efficiency and lifetime.

Hereinafter, synthesis examples of heteroaromatic compounds of the present invention will be described in detail. However, the following examples are only for illustration, and the present invention is not limited thereto.

Synthesis of Compound H06

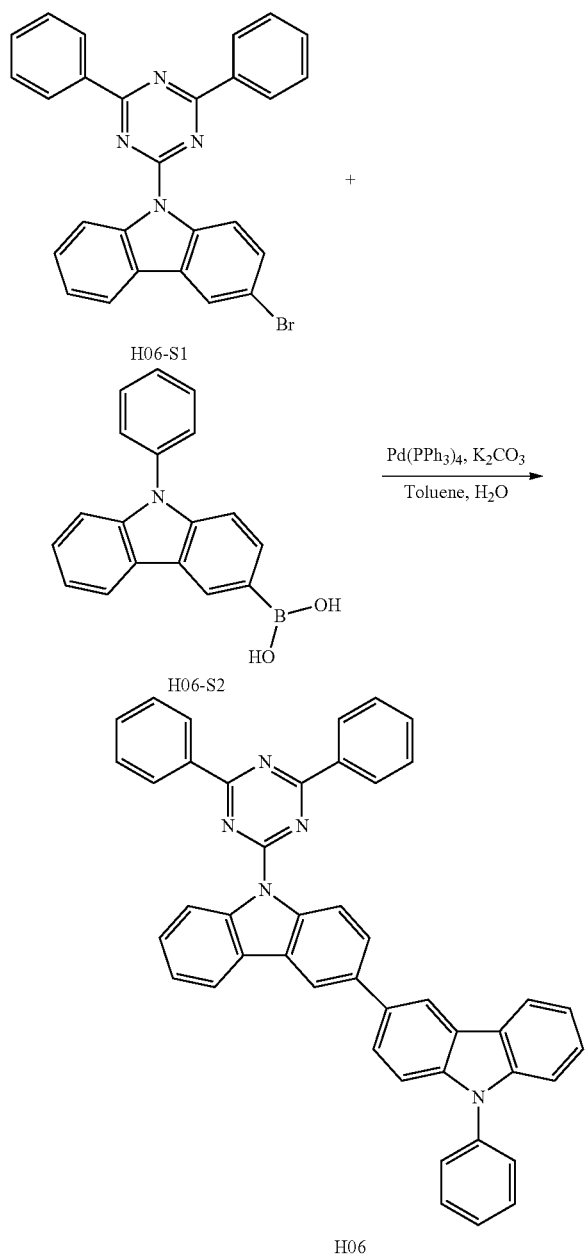

carbonate ($K_2CO_3$) (3.0 mol) were put in the mixture, followed by injection of nitrogen ($N_2$). The mixture was stirred for about 20 minutes to completely dissolve it in a solvent, and then stirred for 24 hours at a temperature set to 130 L. After completion of the reaction, the mixture was worked up with water and methylene chloride, and filtered through a silica gel column, thereby yielding 0.6 mol of Compound H06.

Synthesis of Compound E08

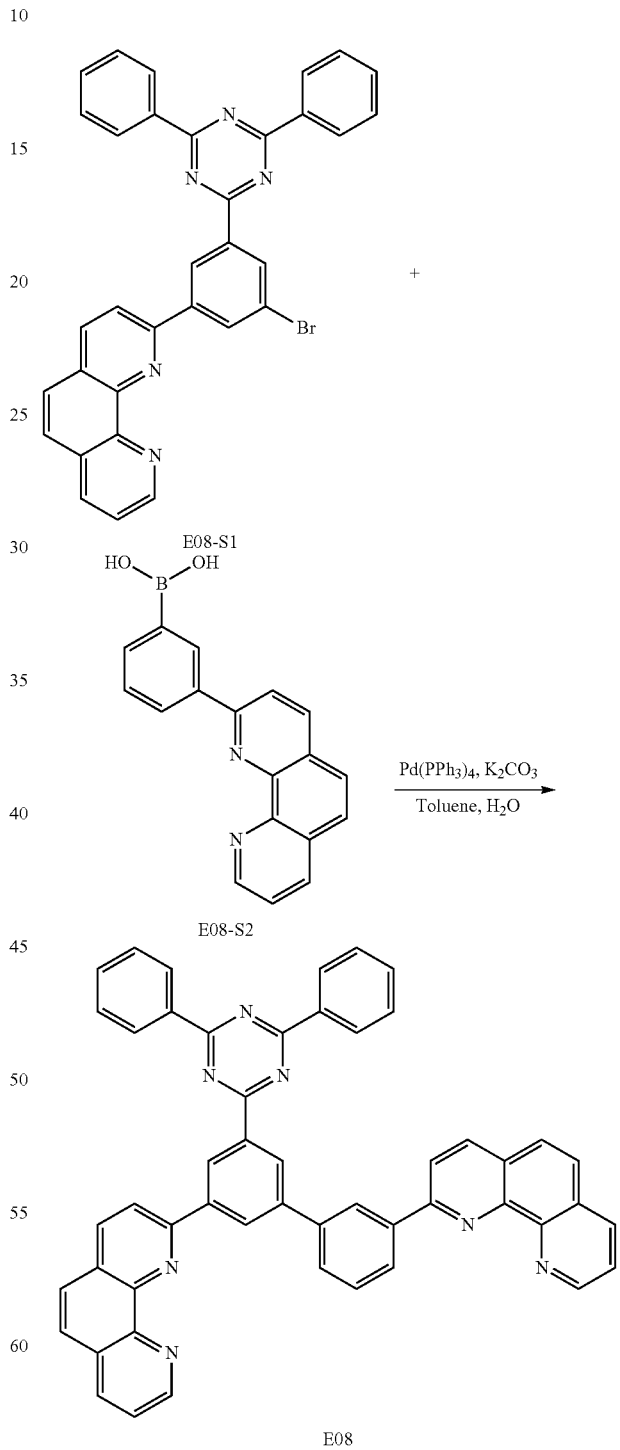

H06-S1 (1.5 mol) and H06-S2 (1.7 mol) were put into a three-necked round-bottom flask, and 50 mol of toluene and 50 mol of water ($H_2O$) were added. Tetrakis(triphenylphosphine)palladium(0) ($Pd(PPh_3)_4$) (0.03 mol) and potassium E08-S1 (2.0 mol) and E08-S2 (2.5 mol) were put into a three-necked round-bottom flask, and 70 mol of toluene and 70 mol of water (H$_2$O) were added. Tetrakis(triphenylphosphine)palladium(0) (Pd(PPh$_3$)$_4$) (0.06 mol) and potassium carbonate (K$_2$CO$_3$) (5.0 mol) were put in the mixture, followed by injection of nitrogen (N$_2$). The mixture was stirred for about 20 minutes to completely dissolve it in a solvent, and then stirred for 24 hours at a temperature set to 130 L. After completion of the reaction, the mixture was worked up with water and methylene chloride, and filtered through a silica gel column, thereby yielding 1.5 mol of Compound E08.

Hereinafter, embodiments for the manufacture of an organic light emitting display device according to the present invention will be disclosed. However, the following materials for the electron transport layer do not limit the scope of this invention.

Comparative Example

An organic light emitting display device was manufactured by forming a hole injection layer, a hole transport layer, an emitting layer, an electron transport layer, an electron injection layer and a cathode on a substrate. The emitting layer was yellow-green emitting layer and was formed of CBP as a host, and the electron transport layer was formed of an anthracene derivative. The device in testing was a mono device.

Embodiment 1

The organic light emitting display device has the same composition as Comparative Example, and the emitting layer includes the following Compound H01 as a host with electron transport properties, and the electron transport layer includes the following Compound E01.

Embodiment 2

The organic light emitting display device has the same composition as Comparative Example, and the emitting layer includes the following Compound H02 as a host with electron transport properties, and the electron transport layer includes Compound E01.

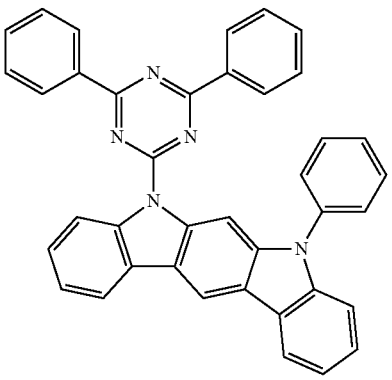

Embodiment 3

The organic light emitting display device has the same composition as Comparative Example, and the emitting layer includes Compound H01 as a host with electron transport properties, and the electron transport layer includes the following Compound E04.

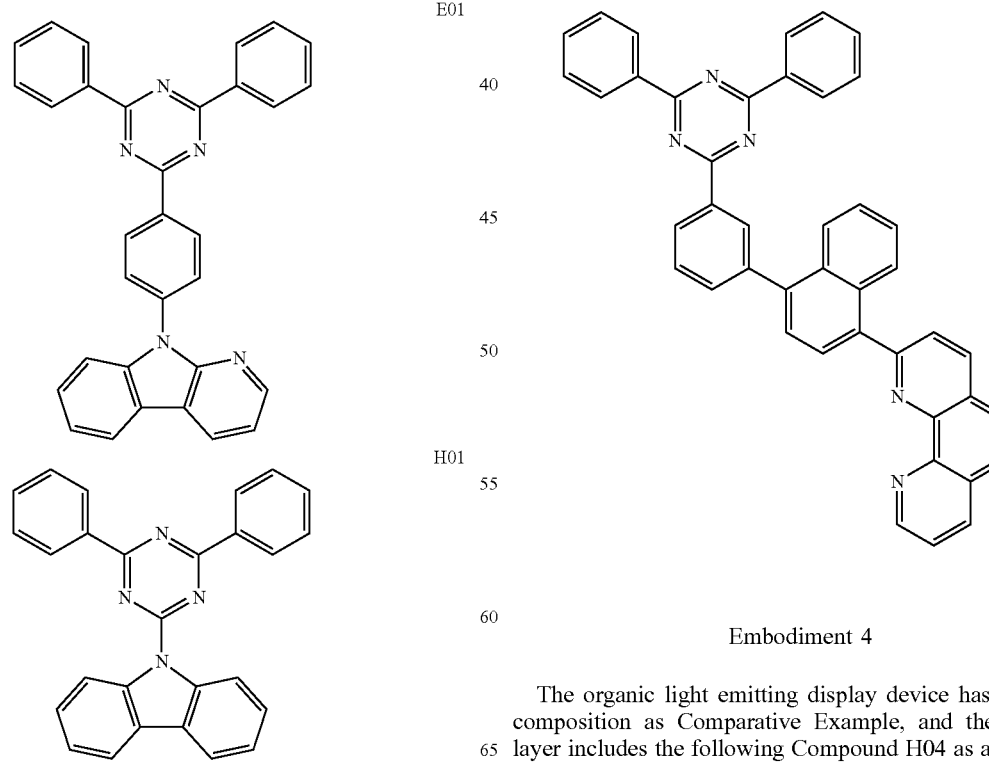

Embodiment 4

The organic light emitting display device has the same composition as Comparative Example, and the emitting layer includes the following Compound H04 as a host with electron transport properties, and the electron transport layer includes Compound E04.

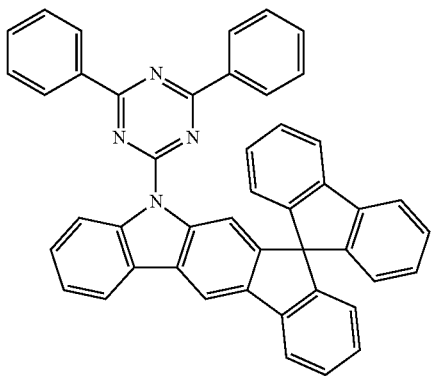

H04

Embodiment 5

The organic light emitting display device has the same composition as Comparative Example, and the emitting layer includes the following Compound H05 as a host with electron transport properties, and the electron transport layer includes Compound E08.

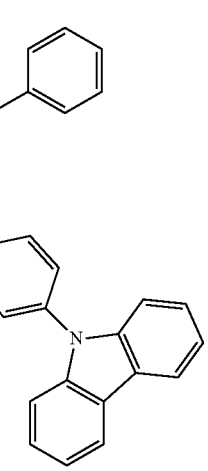

H05

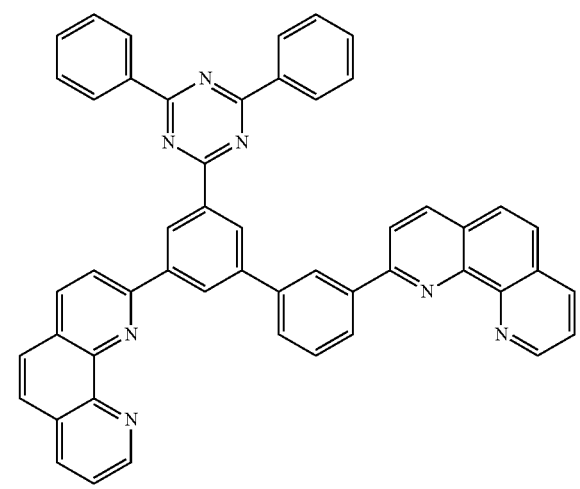

E08

Embodiment 6

The organic light emitting display device has the same composition as Comparative Example, and the emitting layer includes the following Compound H06 as a host with electron transport properties, and the electron transport layer includes Compound E08.

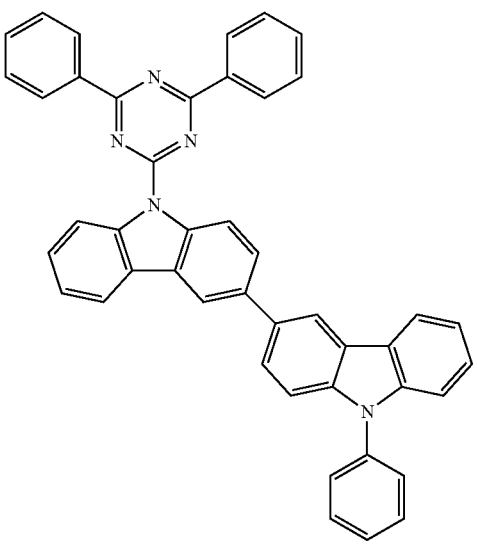

H06

The materials for the emitting layer and electron transport layer in the above Comparative Example and Embodiments 1 to 6 do not limit the scope of this invention.

The operating voltage, external quantum efficiency, and lifetime of the devices according to Comparative Example and Embodiments 1 to 6 were measured and shown in the following Table 1. (The operating voltage, external quantum efficiency, and lifetime measurements taken in the embodiments were expressed as a percentage relative to those taken in the comparative example corresponding to 100%, and the operating current of the device was 10 mA/cm$^2$).

TABLE 1

|  | Operating voltage (%) | External quantum efficiency (%) | Lifetime (%) |
|---|---|---|---|
| Comparative Example | 100 | 100 | 100 |
| Embodiment 1 | 72 | 105 | 250 |
| Embodiment 2 | 73 | 108 | 220 |
| Embodiment 3 | 75 | 109 | 200 |
| Embodiment 4 | 74 | 107 | 210 |
| Embodiment 5 | 70 | 108 | 200 |
| Embodiment 6 | 71 | 111 | 210 |

With reference to Table 1, Embodiment 1 having Compound H01 as a host for the emitting layer and Compound E01 as the electron transport layer showed a 28% decrease in operating voltage, a 5% increase in external quantum efficiency, and a 150% increase in lifetime, compared to Comparative Example 1 having CBP as a host for the emitting layer and an anthracene derivative as the electron transport layer. Also, Embodiment 2 having Compound H02 as a host for the emitting layer and Compound E01 as the electron transport layer showed a 27% decrease in operating voltage, an 8% increase in external quantum efficiency, and a 120% increase in lifetime. Also, Embodiment 3 having Compound H01 as a host for the emitting layer and Compound E04 as the electron transport layer showed a 25% decrease in operating voltage, a 9% increase in external quantum efficiency, and a 100% increase in lifetime. Also, Embodiment 4 having Compound H04 as a host for the emitting layer and Compound E04 as the electron transport layer showed a 26% decrease in operating voltage, a 7% increase in external quantum efficiency, and a 110% increase in lifetime. Also, Embodiment 5 having Compound H05 as a host for the emitting layer and Compound E08 as the electron transport layer showed a 30% decrease in operating voltage, an 8% increase in external quantum efficiency, and a 100% increase in lifetime. Also, Embodiment 6 having Compound H06 as a host for the emitting layer and Compound E08 as the electron transport layer showed a 29% decrease in operating voltage, an 11% increase in external quantum efficiency, and a 110% increase in lifetime.

From these results, it can be found out that the heteroaromatic compounds as a host for the emitting layer and as the electron transport layer reduced the operating voltage and increased the lifetime and external quantum efficiency. Accordingly, it can be concluded that an organic light emitting display device manufactured having the compound achieves a lower operating voltage and a relatively higher lifetime and efficiency, as compared with an organic light emitting display device manufactured without the compound.

As seen from above, the present invention is used a heteroaromatic ring compound including a triazine having 3 electron-rich nitrogen atoms as the electron-type host, thereby improving the property of transporting electrons to the emitting layer.

Also, the present invention is used a heteroaromatic ring compound with electron transport properties as the electron-type host for the emitting layer, thus making the emitting layer rich in electrons, thereby reducing the operating voltage of the device and increasing its efficiency and lifetime.

Moreover, the present invention is used a triazine having 3 electron-rich nitrogen atoms as the electron transport layer, thus improving the property of transporting electrons from the electron transport layer to the emitting layer.

In addition, the present invention is used heteroaromatic ring compounds with the same core are used as the host material for the emitting layer and the material for the electron transport layer, thus allowing the host for the emitting layer and the electron transport layer to have a similar energy level and therefore facilitating electron transport from the electron transport layer to the emitting layer.

Further, the present invention is used heteroaromatic ring compounds with the same core as the host material for the emitting layer and the material for the electron transport layer, thus lowering the electron injection barrier between the electron transport layer and the emitting layer and therefore improving the property of transporting electrons from the electron transport layer to the emitting layer.

Further, the present invention is used heteroaromatic ring compounds with the same core as the host material for the emitting layer and the material for the electron transport layer, thus improving the property of transporting electrons from the electron transport layer to the emitting layer and therefore reducing the operating voltage of the organic light emitting device and increasing its efficiency and lifetime.

It will be apparent to those skilled in the art that various modifications and variations can be made in the organic light emitting display device of the present invention without departing from the spirit or scope of the invention. Thus, it is intended that the present invention cover the modifications and variations of this invention provided they come within the scope of the appended claims and their equivalents.

What is claimed is:

1. An organic light emitting display device, comprising:
a first light emitting part between an anode and a cathode, the first light emitting part having a first emitting layer and a first electron transport layer; and
a second light emitting part over the first light emitting part, the second light emitting part having a second emitting layer and a second electron transport layer,
wherein at least one among the first and second emitting layers comprises a compound among H01, H02, H03, H04, H05, H06, H07 and H08:

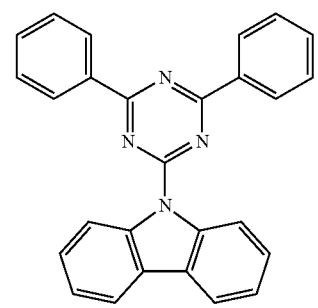

H01

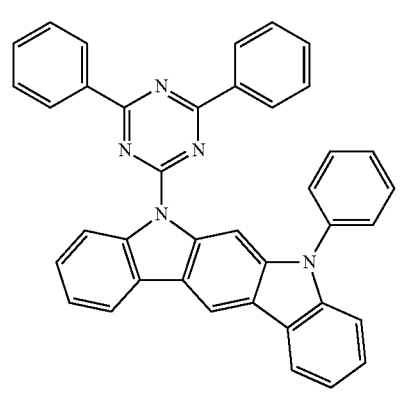

H02

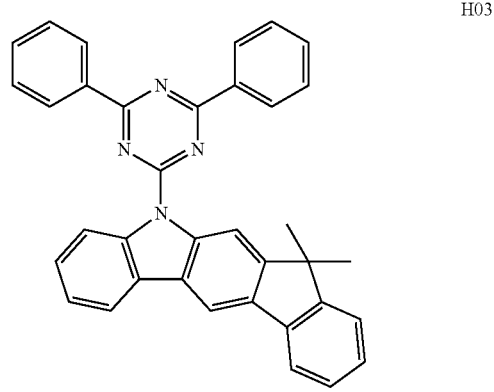

H03

H04
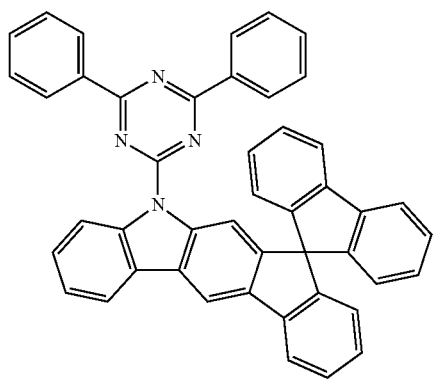
H05
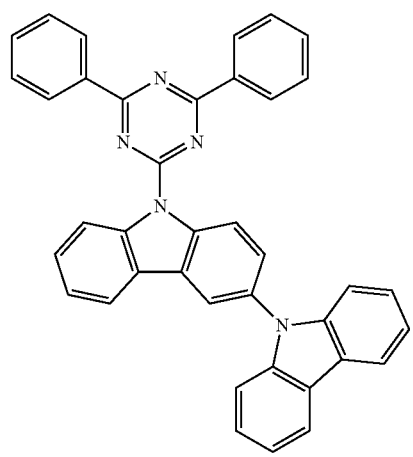
H06
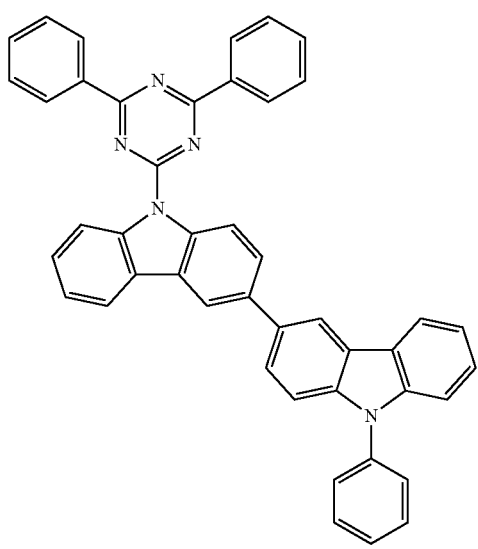
H07
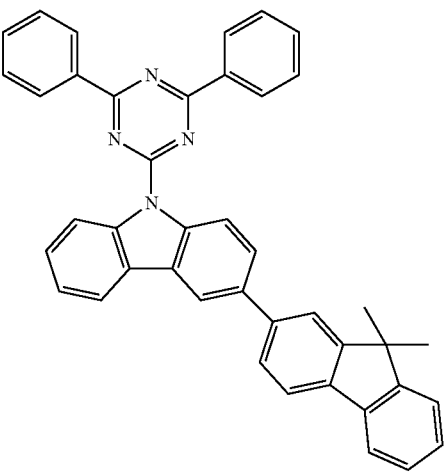
H08
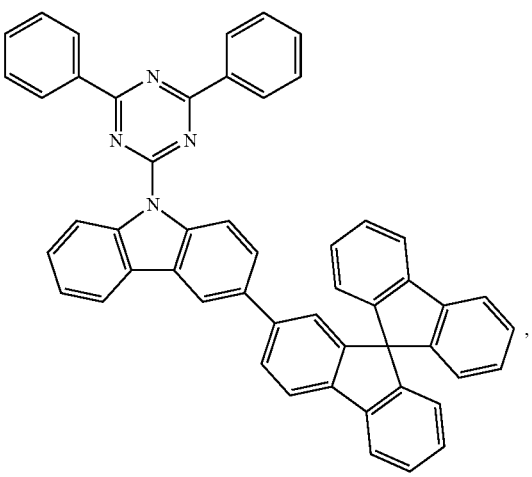
and
at least one among the first and second electron transport layers comprises a compound among E01, E02, E03, E04, E05, E06, E07, E08, E09 and E10:
E01
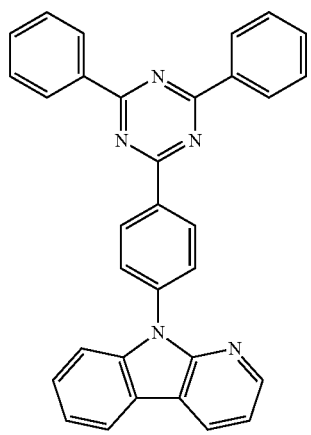

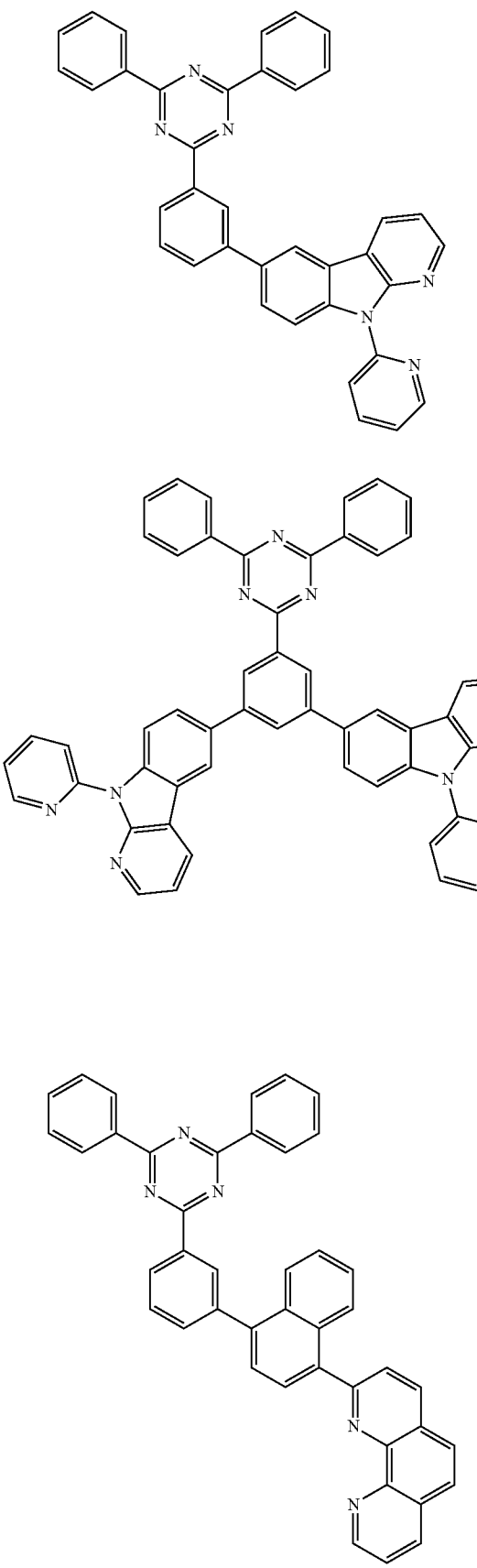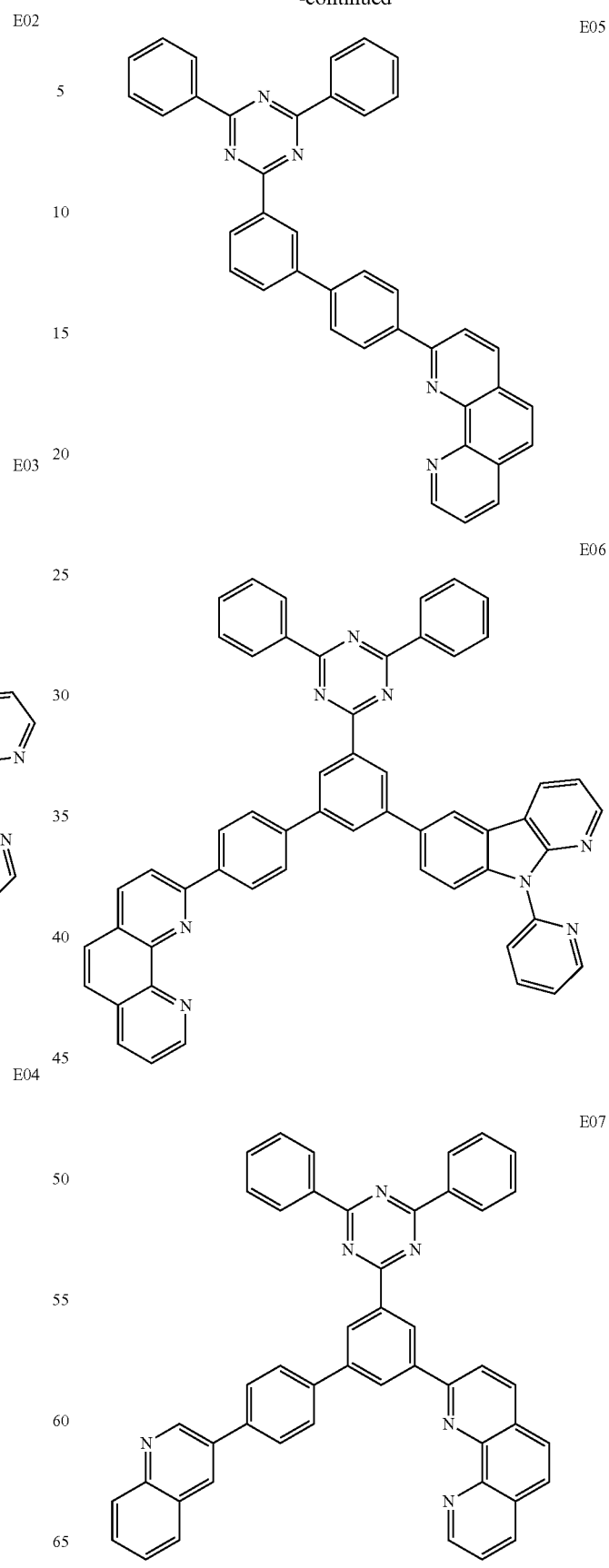

-continued

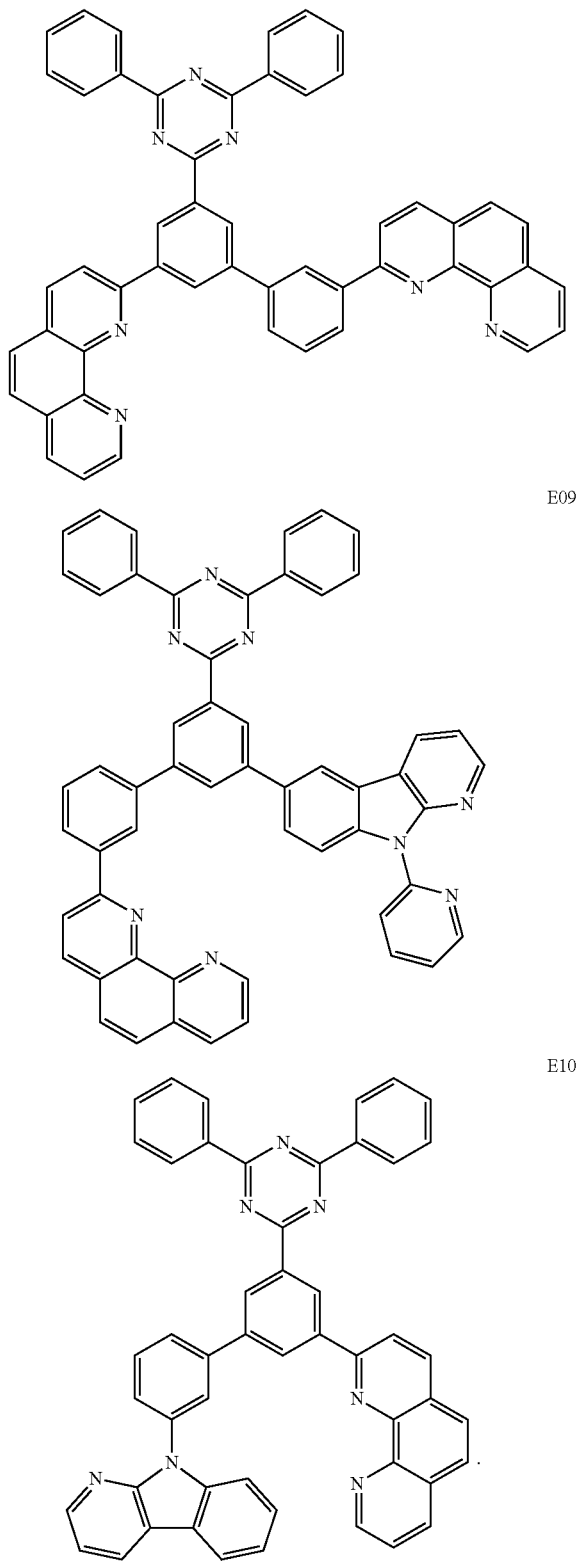

E08

E09

E10

2. The organic light emitting display device of claim 1, wherein the first and second emitting layers each includes an electron-type host and a hole-type host, and the electron-type host of at least one among the first and second emitting layers comprises the compound among H01, H02, H03, H04, H05, H06, H07 and H08.

3. The organic light emitting display device of claim 1, further comprising a third light emitting part over the second light emitting part, the third light emitting part having a third emitting layer and a third electron transport layer,
wherein at least one among the first, second, and third emitting layers comprises the compound among H01, H02, H03, H04, H05, H06, H07 and H08, and at least one among the first to third electron transport layers comprises the compound among E01, E02, E03, E04, E05, E06, E07, E08, E09 and E10.

4. The organic light emitting display device of claim 3, wherein the first, second, and third emitting layers each includes an electron-type host and a hole-type host, and the electron-type host of at least one among the first, second, and third emitting layers comprises the compound among H01, H02, H03, H04, H05, H06, H07 and H08.

5. An organic light emitting display device, comprising:
a light emitting part over an anode, the light emitting part having an emitting layer and an electron transport layer; and
a cathode over the light emitting part,
wherein the emitting layer and the electron transport layer each includes a triazine-containing heteroaromatic ring compound to facilitate electron transport from the electron transport layer to the emitting layer, where the trazine-containing heteroaromatic ring compound of the emitting layer comprises a compound among H01, H02, H03, H04, H05, H06, H07 and H08:

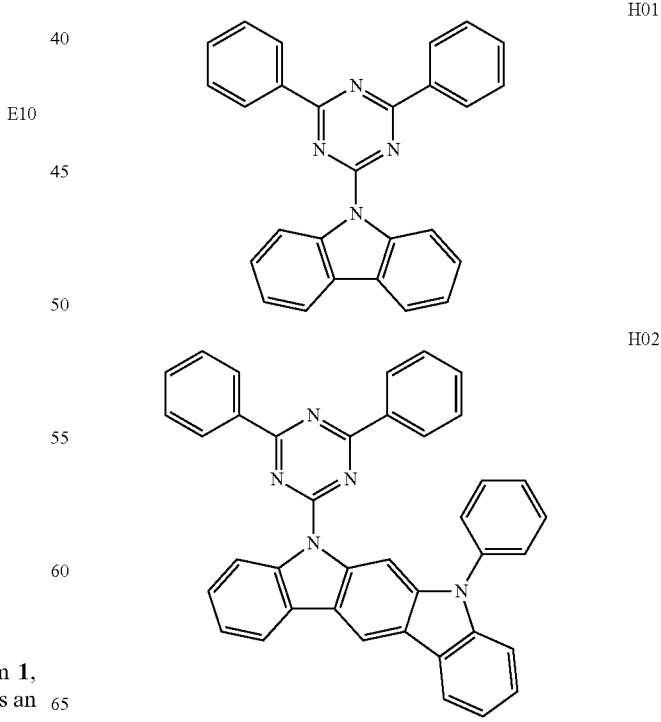

H01

H02

H03
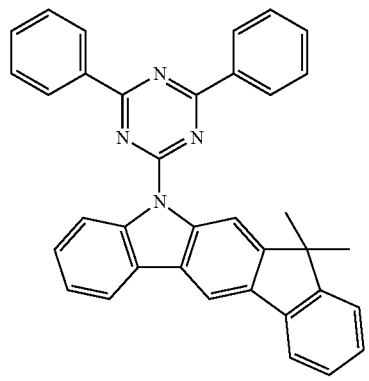
H04
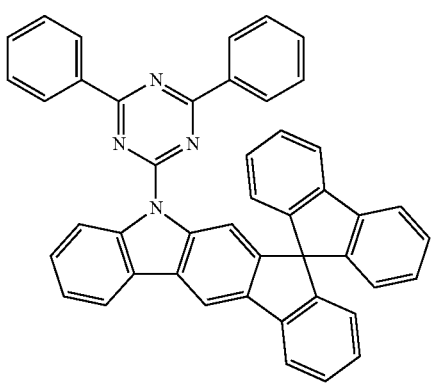
H05
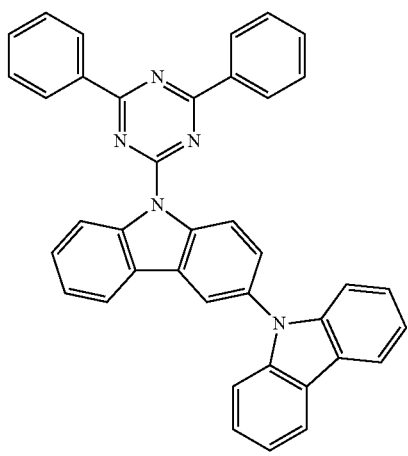
H06
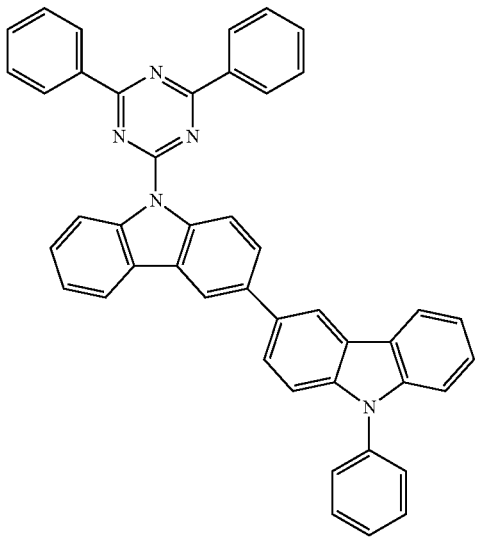
H07
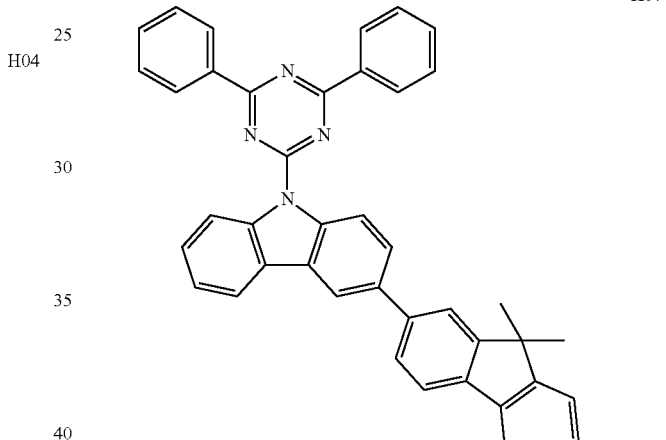
H08
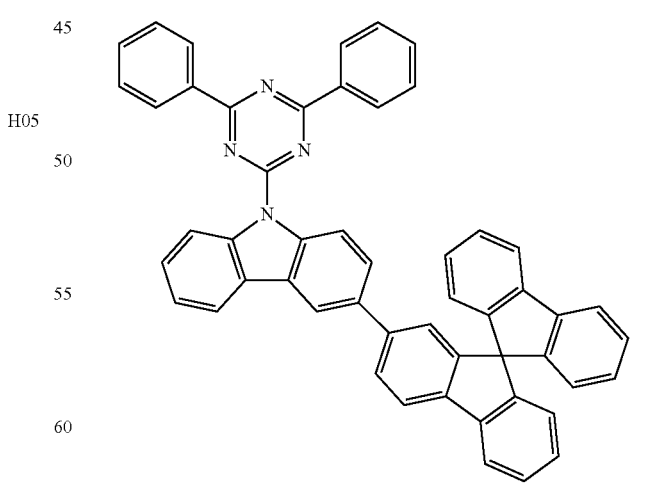
and
the electron transport layer comprises a compound among E01, E02, E03, E04, E05, E06, E07, E08, E09, and E10:

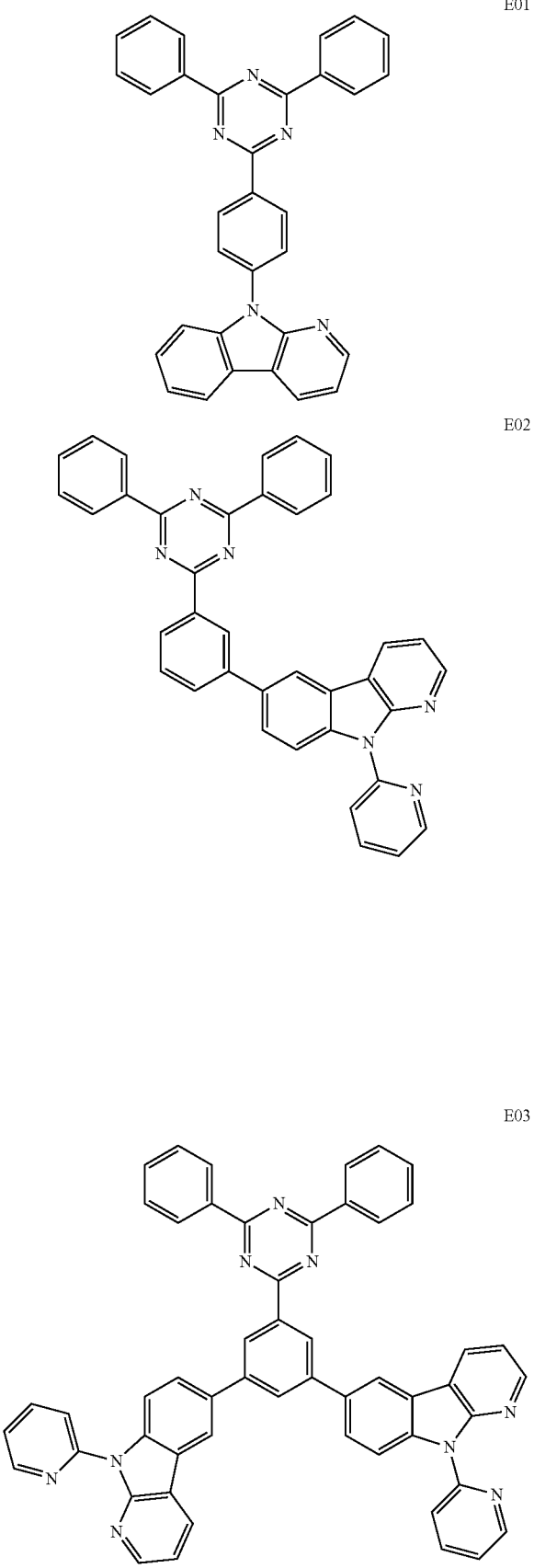
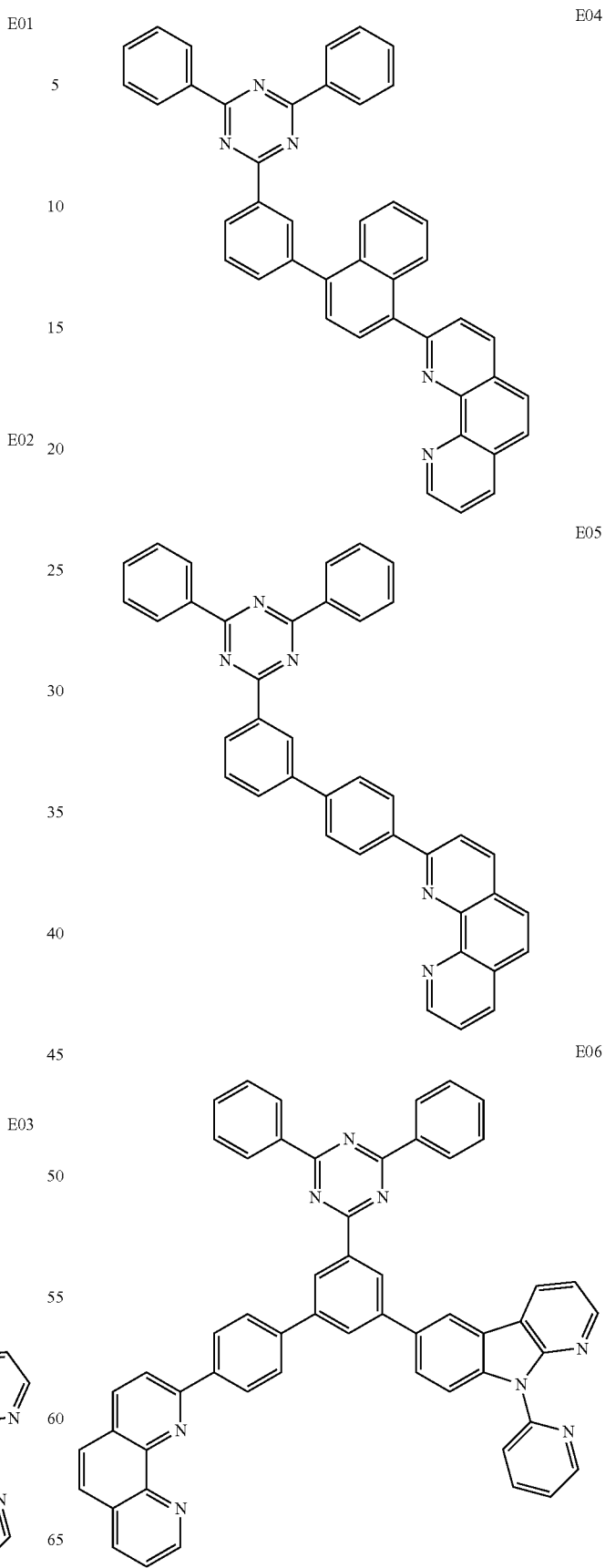

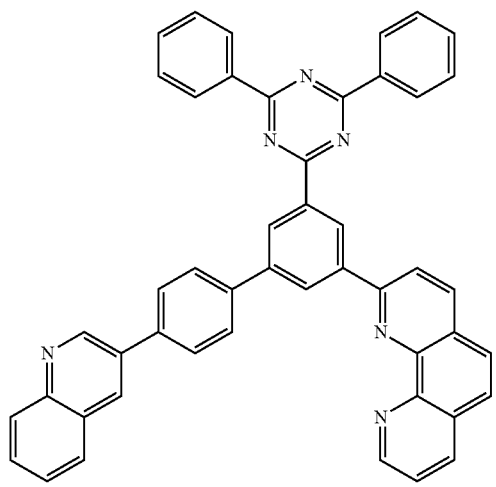
E07

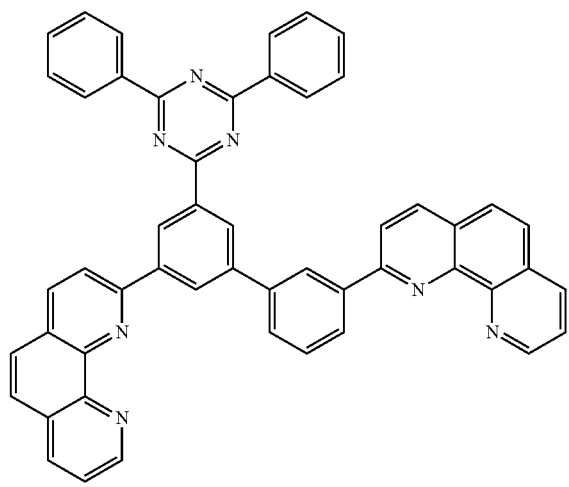
E08

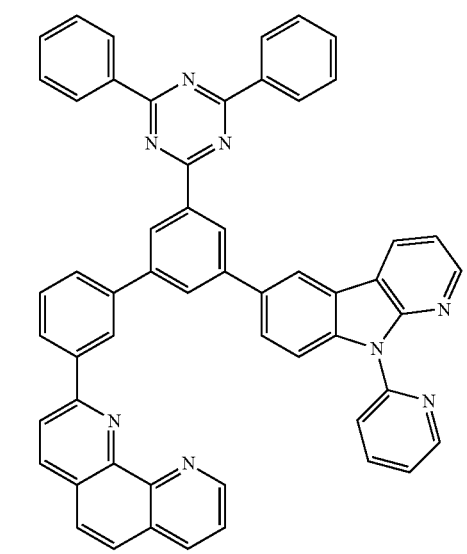
E09

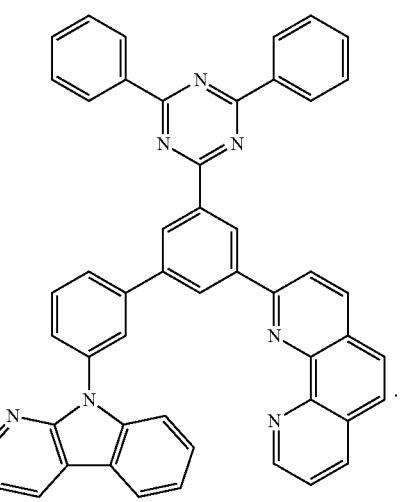
E10

6. The organic light emitting display device of claim 5, wherein the emitting layer includes an electron-type host and a hole-type host, and the electron-type host comprises the compound among H01, H02, H03, H04, H05, H06, H07 and H08.

7. The organic light emitting display device of claim 5, wherein the light emitting part includes:
   a first light emitting part having a first emitting layer and a first electron transport layer; and
   a second light emitting part having a second emitting layer and a second electron transport layer.

8. The organic light emitting display device of claim 7, wherein the second emitting layer includes a yellow-green or green emitting layer, and an electron-type host of the yellow-green or green emitting layer comprises the compound among H01, H02, H03, H04, H05, H06, H07 and H08, and the second electron transporting layer comprises the compound among E01, E02, E03, E04, E05, E06, E07, E08, E09 and E10 to improve the lifetime and efficiency of the yellow-green emitting layer.

9. The organic light emitting display device of claim 8, wherein the light emitting part further includes a third light emitting part, the third light emitting part having a third emitting layer and a third electron transport layer.

* * * * *